United States Patent [19]
Williams

[11] Patent Number: 5,151,081
[45] Date of Patent: Sep. 29, 1992

[54] FOOT SPLINT

[75] Inventor: Paul J. Williams, Tampa, Fla.

[73] Assignee: L'Nard Associates, Inc., Clearwater, Fla.

[21] Appl. No.: 666,370

[22] Filed: Mar. 8, 1991

[51] Int. Cl.⁵ ............................................. A61F 5/00
[52] U.S. Cl. ............................................. 602/27; 602/23
[58] Field of Search .............. 128/80 H, 80 R, 87 R, 128/89 R, 90, 80 E, 83.5

[56] References Cited

U.S. PATENT DOCUMENTS

| | | | |
|---|---|---|---|
| 3,506,000 | 4/1970 | Baker | 128/80 R |
| 3,976,059 | 8/1976 | Lonardo | 128/80 E |
| 4,446,856 | 7/1984 | Jordan | 128/80 H |
| 4,878,504 | 11/1989 | Nelson | 128/80 H |

Primary Examiner—Richard J. Apley
Assistant Examiner—Lynne A. Reichard
Attorney, Agent, or Firm—Zarley, McKee, Thomte, Voorhees & Sease

[57] ABSTRACT

This invention involves a foot splint which utilizes an L-shaped plastic splint element having an upstanding leg portion, a heel portion, and a foot portion extending forwardly from the heel portion. A suitable padding material is located on the inside surface of the plastic splint element. A first strap having a figure eight configuration extends from the upper outside portion of the plastic splint element forwardly and downwardly around the bottom of the foot portion, with segments of the strap overlapping each other in spaced relation above the foot portion. The strap is link adjustable for tightening about the foot of the patient. A stabilizer bar is pivotally secured by its upper end to the upper outside surface of the leg portion and is adapted to be pivotally moved in a transverse direction with respect to the leg portion. A pivotal fastener connects the stabilizer bar to the plastic element and is preloading frictionally so that the stabilizer bar under normal conditions will stay at any angle with respect to the plastic splint element to which it is manually moved.

3 Claims, 2 Drawing Sheets

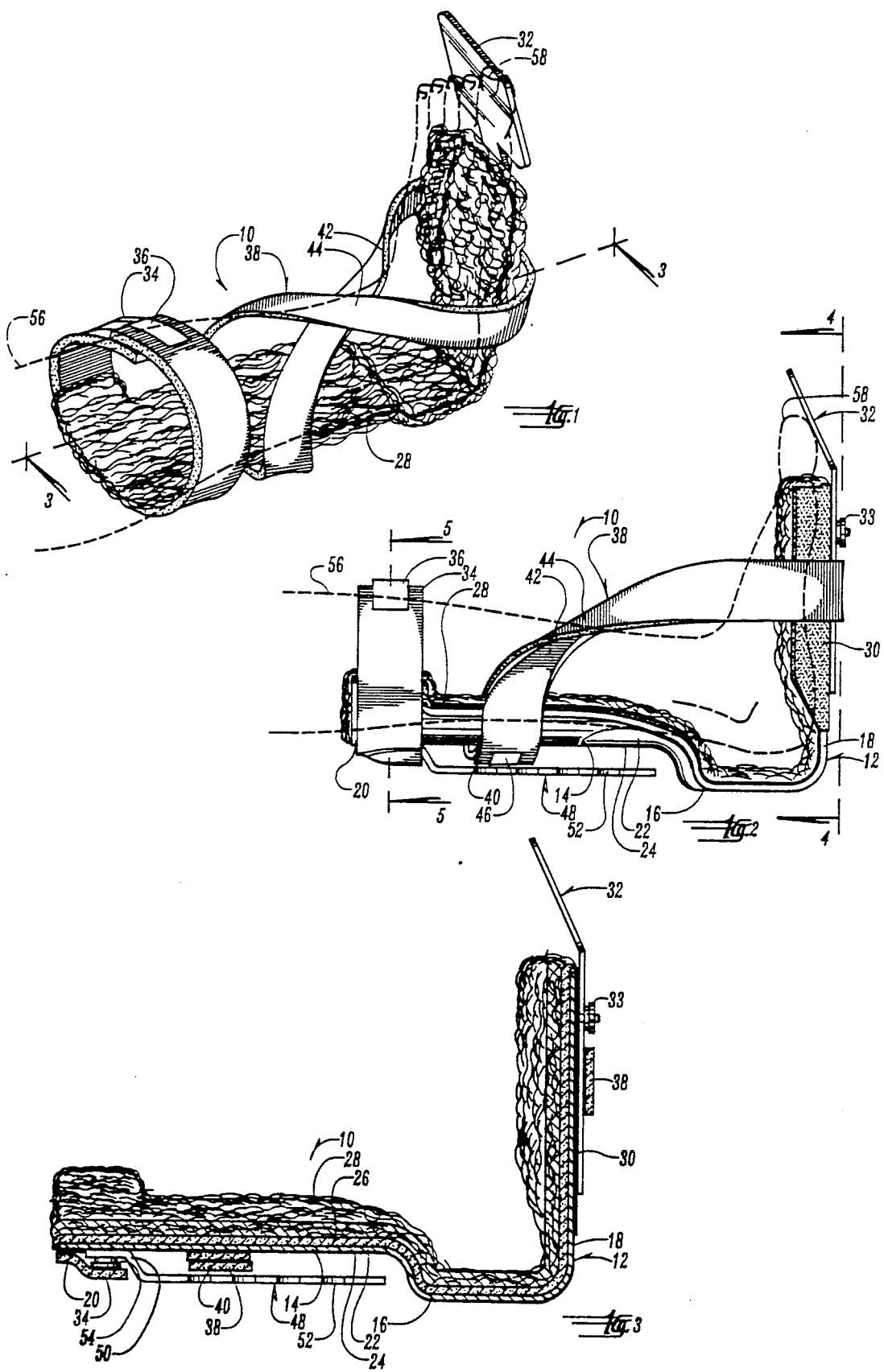

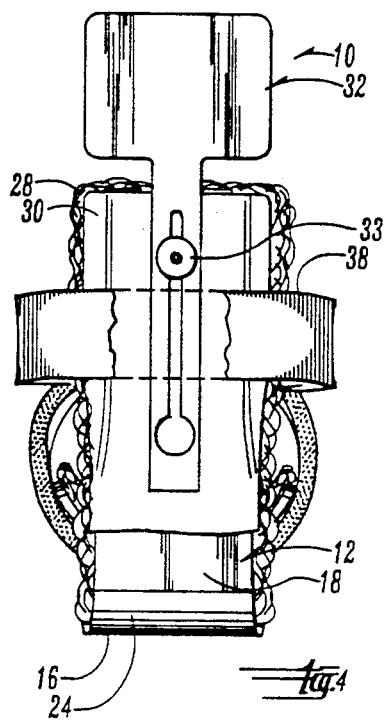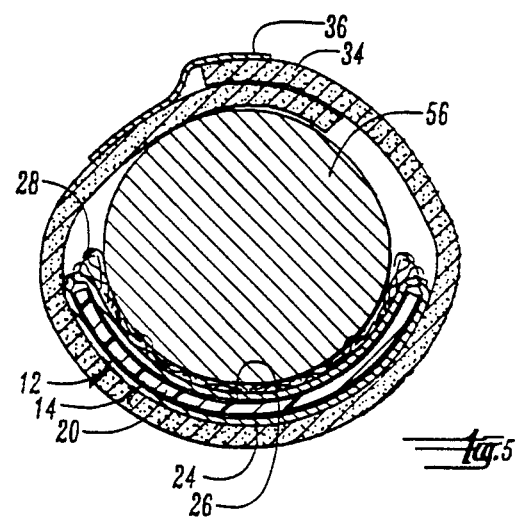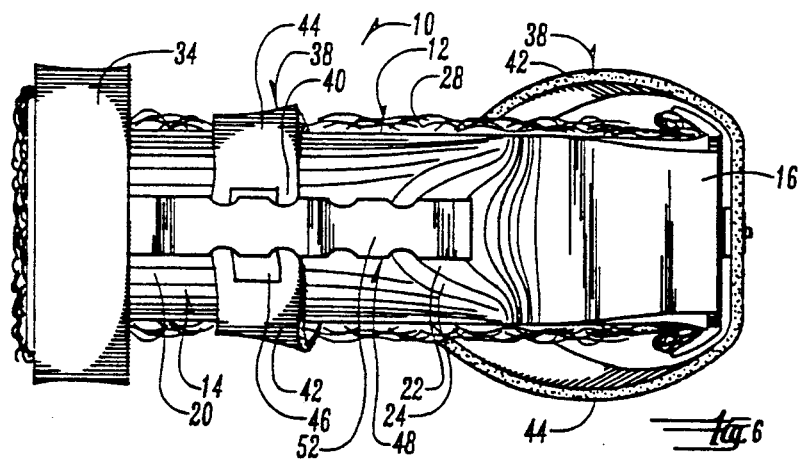

FOOT SPLINT

BACKGROUND OF THE INVENTION

A variety of foot splints are used in the art to provide assistance to bedfast patients who develop sores and other debilitating problems with their feet. A typical splint is shown in U.S. Pat. No. 3,976,059.

Foot splints of the prior art normally include an L-shaped plastic splint element which uses a padded anklet or the like with fasteners thereon to secure the splint element to the patient's foot and lower leg. These anklets are expensive to manufacture; have a limited useful life; and do not always lend themselves for ease of operation in applying the splint device to, or removal from, the patient's foot.

Conventional foot splints also have utilized stabilizer bars secured to the back of the splint element for deployment in a transverse direction from the plastic splint to maintain the attitude of the patient's foot in a predetermined position. These stabilizer bars of the prior art are normally secured to the plastic splint by their lower ends, and usually have a tightening mechanism which must be loosened and then tightened as the stabilizer bar is moved to the desired position.

It is therefore a principal object of this invention to provide a foot splint which can be easily attached to or detached from the foot of a patient without the employment of the use of a conventional anklet means to envelop the foot of the patient.

A further object of this invention is to provide a foot splint with an attachment means that is less expensive to manufacture and easier to operate than the conventional anklet means of existing splints.

A still further object of this invention is to provide a foot splint which has a stabilizer bar pivotally secured to the upper portion of the foot splint to improve the leverage that it can exert on the leg of the patient when deployed in an operational position.

A still further object of this invention is to provide a stabilizer bar for a foot splint that does not need to be manually loosened and tightened as it is deployed to its operational position.

These and other objects will be apparent to those skilled in the art.

SUMMARY OF THE INVENTION

This invention involves a foot splint which utilizes an L-shaped plastic splint element having an upstanding leg portion, a heel portion, and a foot portion extending forwardly from the heel portion. A suitable padding material is located on the inside surface of the plastic splint element. A first strap having a figure eight configuration extends from the upper outside portion of the plastic splint element forwardly and downwardly around the bottom of the foot portion, with segments of the strap overlapping each other in spaced relation above the foot portion. The strap is length adjustable for tightening about the foot of the patient.

A stabilizer bar is pivotally secured by its upper end to the upper outside surface of the leg portion and is adapted to be pivotally moved in a transverse direction with respect to the leg portion. A pivotal fastening means connects the stabilizer bar to the plastic splint element and is preloaded frictionally so that the stabilizer bar under normal conditions will stay at any angle with respect to the plastic splint element to which it is manually moved.

BRIEF DESCRIPTION OF THE DRAWINGS

FIG. 1 is a perspective view of the foot splint of this invention;

FIG. 2 is a side elevational view thereof;

FIG. 3 is a sectional view taken on line 3—3 of FIG. 1;

FIG. 4 is a bottom elevational view taken on line 4—4 of FIG. 2;

FIG. 5 is a sectional view taken on line 5—5 of FIG. 2; and

FIG. 6 is a rear elevational view thereof.

DESCRIPTION OF THE PREFERRED EMBODIMENT

The foot splint 10 includes a plastic splint element 12 having a back portion 14, a heel portion 16, and a foot portion 18. The splint element 12 is preferably comprised of a stiff but resilient material and is of integral construction. The back portion 14 has an upper end 20 and a lower end 22. The splint element 12 has an outside surface 24 and an inside surface 26.

A suitable padding material 28 secured to a backing layer 30 (FIG. 2) is mounted on the inside surface 26 of splint element 12 in any convenient manner. A conventional toe plate assembly 32 is secured by fastener 33 (FIG. 2) to the lower surface of the foot portion 18.

A horizontal strap 34 is secured in any convenient manner to the upper end 20 of back portion 14. A conventional VELCRO ® fastener 36 permits the free ends of strap 34 to be securely wrapped and fastened around the lower leg portion of a patient wearing the foot splint 10.

An elongated strap 38 is used to secure the splint element 12 to the foot and leg of a patient. Strap 38 normally assumes the figure eight configuration shown in FIG. 1 when the splint is mounted on the foot of a patient. Strap 38 extends from a point of beginning 40 towards the upper end 20 of back portion 14 on the outside surface 24 thereof. A first segment 42 extends downwardly and forwardly over and across the foot portion 18, thence underneath the foot portion, and continues in second segment 44 which extends upwardly and over foot portion 18 back to the point of beginning 40. The segments 42 and 44 are in spaced relation to the splint element 12 so as to accommodate the foot of the patient. A VELCRO ® fastener 46 accommodates the ends of strap 38 so that the strap is length adjustable for purposes of snugly securing the strap and the splint element to the foot of the patient.

A stabilizer bar 48 has an offset portion 50 at its upper end, which terminates in an elongated portion 52 at its other end. The offset portion 50 is pivotally secured to the upper end 20 of back portion 44 on the outside surface 24 thereof. Frictional pivotal mounting means 54 secures the stabilizer bar to the splint element 12 and is adapted to maintain the angular position of the stabilizer bar with respect to the splint element as determined by the angular position to which the stabilizer bar is moved by the person attending the patient.

In operation, the straps 34 and 38 are released to receive the patient's foot into the splint. The horizontal strap 34 is then secured around the leg of the patient and pulled and held to a snug position by the fastener 36. The strap 38 is then assembled over the patient's foot and upper leg in the figure eight configuration shown in FIG. 1. The strap 38 is pulled to and held in a snug position by means of the fastener 46. As a result, the splint 10 can be easily and quickly secured to and removed from the foot of the patient. The strap 38 is much less expensive than the typical anklet used with splints of the prior art.

By being pivotally secured by its upper end, the stabilizer bar 48 is more convenient to operate. The frictional pivoted mounting means 54 eliminates the separate loosening and tightening functions of stabilizer bars of prior art splints. When the stabilizer is turned transversely to the splint, the patient is inhibited from the turning of their leg in the direction of the stabilizer bar.

Accordingly, it is seen that the device of this invention will achieve at least its stated objectives.

I claim:

1. A foot splint, comprising:
   an L-shaped plastic splint means comprising an upstanding leg portion having inner and outer surfaces, opposite sides and upper and lower ends, a heel portion contiguous with the lower end of said leg portion, and a generally horizontal foot portion having opposite sides and extending forwardly from said heel portion, and
   a stabilizer bar pivotally secured to the upper end of said leg portion on the outside surface thereof, and being pivotally movable between an inoperative position extending downwardly along the outside surface of said leg portion and an operative position extending transversely to the leg portion.

2. The foot splint of claim 1 wherein a fastener means interconnects said stabilizer bar and said leg portion, said fastener means frictionally maintaining said stabilizer bar in an angular position with respect to said leg portion to which said stabilizer bar is manually moved.

3. A foot splint, comprising:
   an L-shaped plastic splint means comprising an upstanding leg portion having an inner and outer surfaces, opposite sides and upper and lower ends, a heel portion contiguous with the lower end of said leg portion, and a generally horizontal foot portion having opposite sides and extending forwardly from said heel portion,
   a securing strap means on said splint means and extending from a point of beginning on the outer surface of said leg portion, thence downwardly and forwardly in spaced relation over and across said foot portion, thence around and underneath said foot portion, thence upwardly in spaced relation and across said foot portion back to said point of beginning,
   and a stabilizer bar pivotally secured to the upper end of said leg portion on the outside surface thereof, and extending downwardly along the outside surface of said leg portion in its inoperative condition.

* * * * *